United States Patent [19]

Martin

[11] Patent Number: 4,839,144
[45] Date of Patent: Jun. 13, 1989

[54] SUPPORT DEVICE FOR COMBUSTIBLE PACKAGE CONTAINING A HEAT-DISPERSIBLE MATERIAL AND A COMBUSTIBLE MATERIAL

[75] Inventor: John Martin, Racine, Wis.

[73] Assignee: S. C. Johnson & Son, Inc., Racine, Wis.

[21] Appl. No.: 82,157

[22] Filed: Aug. 6, 1987

[51] Int. Cl.⁴ ............................ A61L 9/02; A61L 9/03
[52] U.S. Cl. ................................. 422/305; 43/127; 206/524.3; 206/607; 211/73; 239/57; 248/166; 422/126; 422/306; 424/405; 424/40; 431/343
[58] Field of Search ................. 422/305, 306, 126; 43/125, 127, 144; 206/0.5, 524.3, 216, 605, 607; 29/163.5 R, DIG. 3, DIG. 33; 424/76, 405, 406; 431/154, 343; 239/57; 248/174, 166; 211/73; 44/541

[56] References Cited

U.S. PATENT DOCUMENTS

| | | |
|---|---|---|
| 813,323 | 2/1906 | Rivers . |
| 1,053,873 | 2/1913 | Reenstierna ..................... 422/126 |
| 1,806,149 | 5/1931 | Daugherty ...................... 206/0.5 |
| 2,054,703 | 9/1936 | Little et al. .................... 29/163.5 R |
| 2,132,786 | 10/1938 | Hockenyos . |
| 2,189,730 | 2/1940 | Esch . |
| 2,253,111 | 8/1941 | Cronstrom ...................... 206/216 |
| 2,765,579 | 10/1956 | Gordon . |
| 2,896,853 | 7/1959 | Curran ........................... 206/0.5 |
| 3,057,470 | 10/1962 | Heiber . |
| 3,071,307 | 1/1963 | Keller . |
| 3,143,059 | 8/1964 | Sofio ............................. 211/73 |
| 3,144,129 | 8/1964 | Weisberg . |
| 3,279,118 | 10/1966 | Allen . |
| 3,689,291 | 9/1972 | Draper ........................... 206/0.5 |
| 4,033,489 | 7/1977 | Fowler ........................... 211/73 |
| 4,096,948 | 6/1978 | Kuchenbecker .................. 206/0.5 |
| 4,171,340 | 10/1979 | Nishimura et al. . |
| 4,330,506 | 5/1982 | Takei . |
| 4,340,168 | 7/1982 | Webinger ........................ 206/0.5 |
| 4,724,593 | 2/1988 | Lang ............................. 29/163.5 R |

Primary Examiner—Michael S. Marcus
Assistant Examiner—Timothy M. McMahon

[57] ABSTRACT

A device for supporting a combustible package containing a heat-dispersible material and a combustible material while the package is consumed fabricated from a single rectangular sheetmetal blank. The blank includes a center area extending across the width of the blank defined by two spaced-apart center scorelines. End sections which are mirror images of each other extend from the center scoreline to the respective end of the rectangular sheetmetal blank. Each end section includes a rectangular inner portion which is bound on two sides and one end by the outer portion, and on the other end by the center area. The center area is fixedly attached to the one end of the inner portion and to the outer portion. The device is fabricated by folding the inner portions upward into a parallel position to provide a space therebetween for holding a combustible package. The outer portions are folded downward at a slant to form legs to support the device and to provide a space between the package being consumed and the surface upon which it rests. The device is of simple construction. In a modified form of the invention the support device in assembled form is adhered to a folded paperboard whereby the device in assembled but folded form is conveniently displayed.

20 Claims, 3 Drawing Sheets

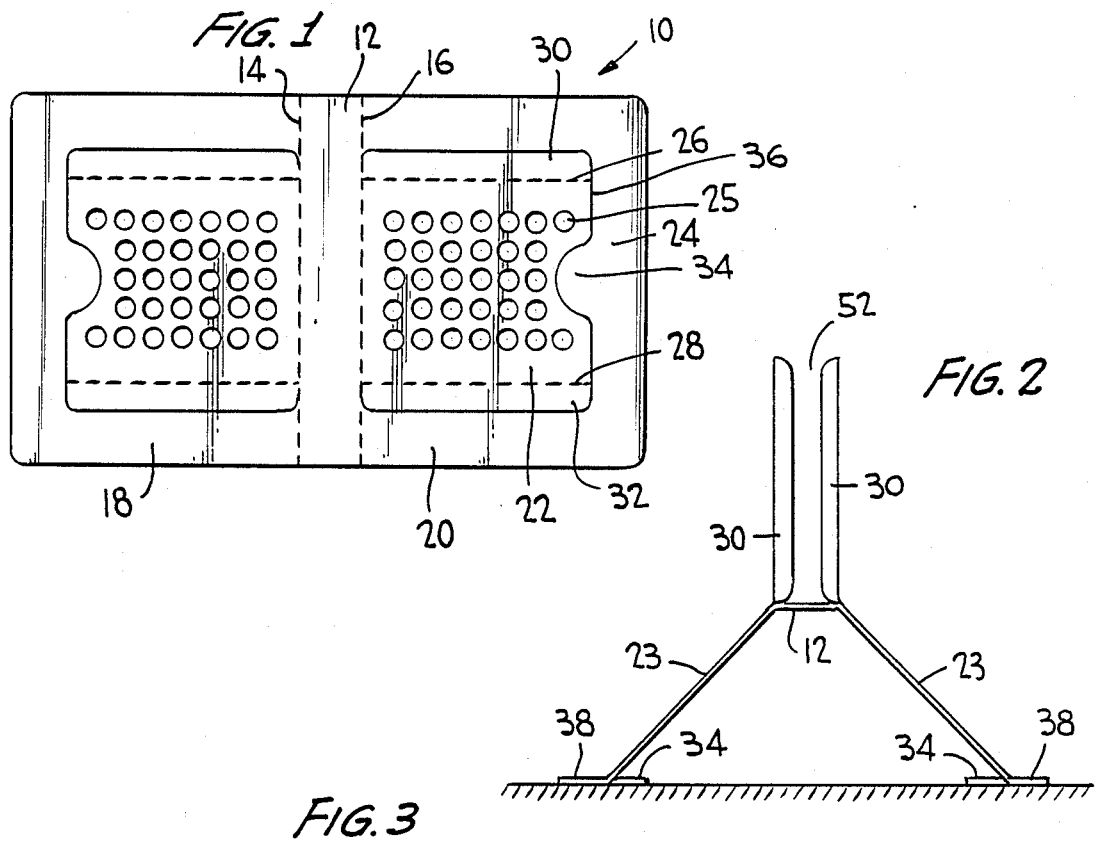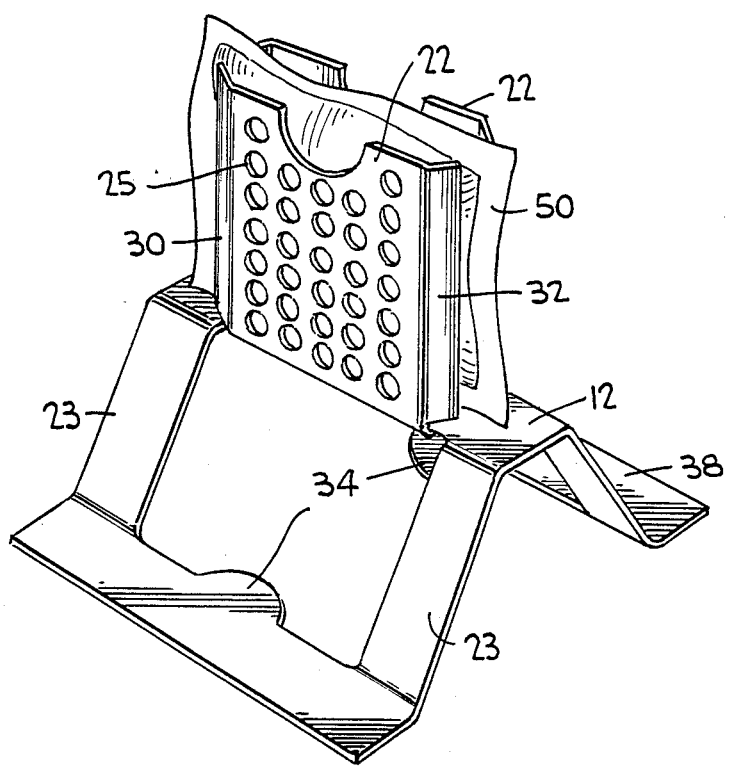

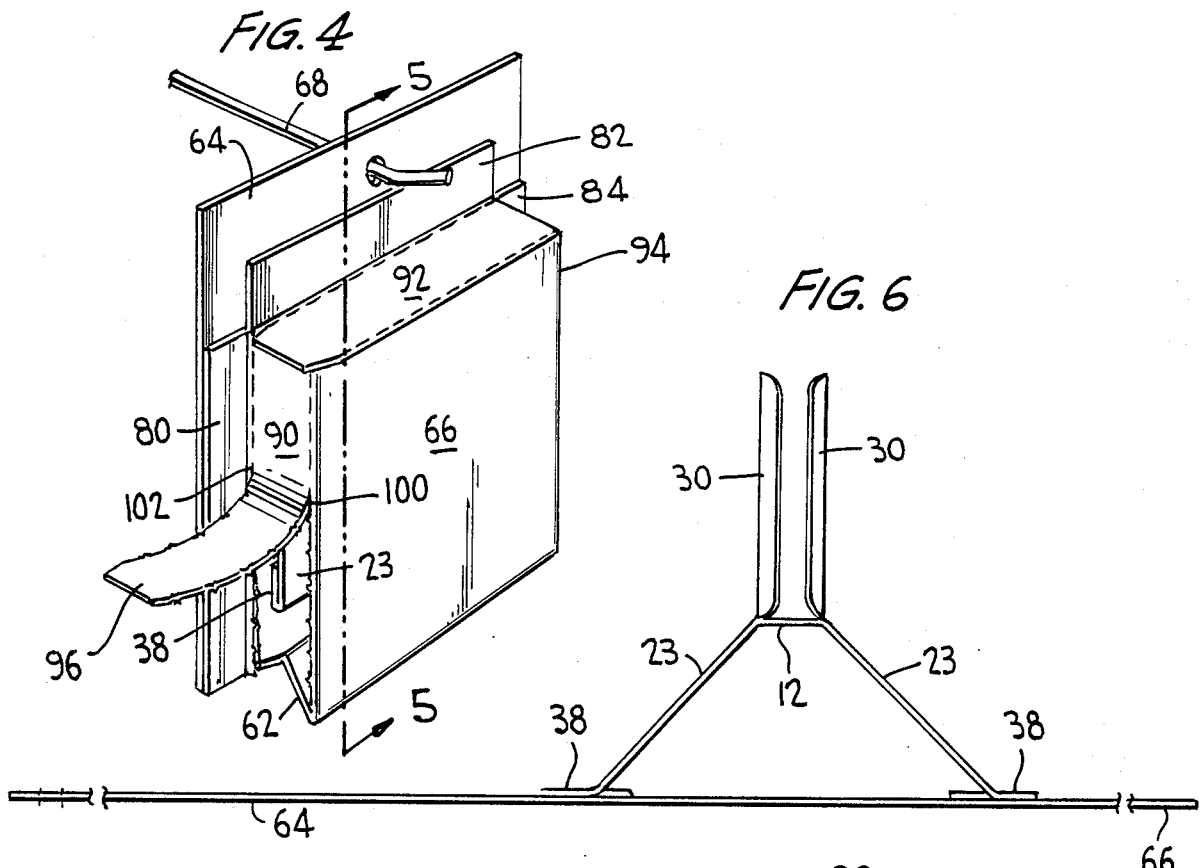
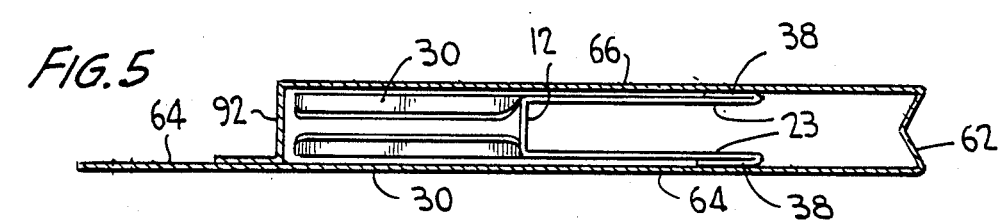
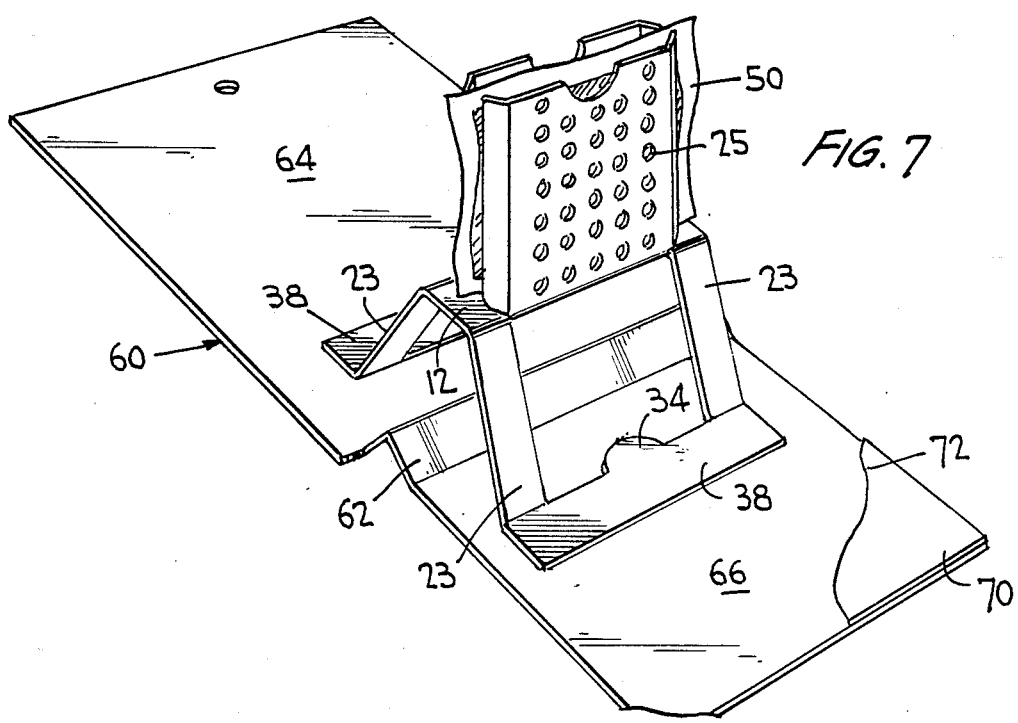

SUPPORT DEVICE FOR COMBUSTIBLE PACKAGE CONTAINING A HEAT-DISPERSIBLE MATERIAL AND A COMBUSTIBLE MATERIAL

FIELD OF INVENTION

This invention relates to devices for dispersing gaseous fluids such as insecticides, fumigants, deodorants, or the like. More particularly, the invention relates to a device for supporting a combustible package while being consumed containing a combustible material and a heat-dispersible material such as an insecticide, fumigant, deodorant, or the like which is to be dispersed into the atmosphere as the package is subjected to combustion.

BACKGROUND OF INVENTION

The desirability of dispensing a material such as an insecticide, fumigant, deodorant, or the like into a confined space such as a room in order to control vermin, insects such as mosquitoes, flies, cockroaches and the like, or to deodorize or disinfect a room as a vapor is well-known. It is also recognized that an effective way of dispersing such materials is by packaging a blend of the heat-dispersible material with a combustible material, and subjecting the package to combustion at time of use to enhance the vaporization of the dispersible material. The prior art has also recognized the desirability of fabricating devices for supporting a combustible package containing the combustible material and heat-dispersible material while the package is being consumed to freely release the dispersible material and to protect a surface carrying the device which is of simple construction. Thus, U.S. Pat. No. 4,171,340 discloses a mixture of a dispersible material such as an insecticide, fungicide, antiseptic or the like, and a blowing agent. The mixture is heated indirectly with heat evolved by contacting an exothermic substance with water to decompose the blowing agent and to volatilize a dispersible material. The mixture is contained in at least one compartment of a container while the exothermic substance is contained in a further compartment provided with water or means for supplying water. The compartments are separated from each other by a partition which provides a heat-transferring surface.

U.S. Pat. No. 4,330,506 describes a thermoevaporative insecticidal apparatus comprising a heat-generating element which is closely fitted to a porous carrier. The surface of the carrier is impregnated with a dispersible ingredient. A receptacle is provided for holding and heating the porous carrier.

U.S. Pat. No. 2,132,786 discloses a process of and composition for generating sulfur dioxide for fumigation purposes in which formation of deposits of solid sublimed sulfur upon the surface of, and chemical decomposition of the articles to be fumigated is avoided. According to this patent, a suitable imflammable compound of sulfur is burned in the presence of carbon dioxide rather than burning elemental sulfur. Burning is effected by incorporating the carbon bisulfide or the like with a porous material such as kieselguhr or cotton batting which acts as an absorbent and thus prevents unduly rapid combustion. Combustion is carried out in a container such as an ordinary tin can.

U.S. Pat. No. 3,279,118 discloses an apparatus for vaporizing insecticides utilizing a sealed pouch containing an insecticide and a stand for holding the sealed pouch. A heating device, such as a lit candle, is placed beneath the stand to heat and thereby vaporize the insecticide within the pouch. The legs of the stand can be secured to a base plate by folding a tab at the bottom of two of the legs around the edge of the base plate. The stand can be made of metal. The pouch can be adhered to the stand by any suitable type of adhesive so that pouch and stand can be handled as a unit.

U.S. Pat. No. 2,765,579 discloses an insect repellent device comprising a package which can be unfolded to expose a wick-type fumer. The fumer package has a lining of heat reflective material, such as metallic foil, to direct the heat upward and outwardly away from the package when the fumer is in operation. Additionally, the package contains an expansion coil spring under the screen holding the fumer. The coil spring expands and elevates the screen above the heat reflecting surface when the package is opened to provide a space between the heat reflective surface of the package and the undersurface of the wick to ensure circulation of air and the dissemination of the fumes from the device. The package is reusable until the entire wick has been consumed by smoldering.

U.S. Pat. No. 2,189,730 discloses an apparatus for evaporating a vermin killing agent consisting of a flat hollow box having a bottom or cover which can be folded back and bent over the box sides to serve as a support for the box. An evaporatable material is contained within the box.

U.S. Pat. No. 3,071,307 discloses a carton for packaging and heating subsistence items. The carton holds a packet which contains the subsistence item to be heated. The carton is formed from a foldable blank. At the time of sale, the carton is already folded into the form of a rectangular package and contains the subsistence packet therein. When the carton is to be utilized to heat the material in the packet, the lid of the carton is folded back and around the ends of the carton to form a support stand for the carton. A suitable heat source, such as fuel tablets, are placed beneath the carton to heat the material. The carton ca be made of fluid-tight and fire-resistant material such as a laminated paperboard-metal foil material.

U.S. Pat. No. 813,323 discloses a fumigating material shaped into interconnecting slabs which are foldable to form a hollow block. The block is placed upon one end and ignited causing fumigating vapor to emanate from the block. The contacting edges of the slab can be joined by glue, paste, or the like.

Accordingly, the prior art discloses a combustible package containing a heat-dispersible material and a combustible material utilized with a support device, including devices which are unfoldable to form a support device. The use of a heat-reflecting material on the upward facing surface of a base is also suggested. However, all of these devices are relatively complex and/or not convenient from the standpoint of use or desirable from the standpoint of sales appeal.

OBJECTS AND GENERAL DESCRIPTION OF INVENTION

Accordingly, a primary object of the present invention is to provide a support device for a combustible package containing a combustible material and a heat-dispersible material while being consumed which is compact, made of lightweight relatively inexpensive materials, and simple in construction.

It is another primary object of this invention to provide a blank for fabricating at time of use a support device for a combustible package containing a combustible material and a heat-dispersible material while being consumed which is inexpensive and simple, and can be conveniently assembled by an ultimate user.

It is another primary object of this invention to provide a pre-formed support device for a combustible package containing a combustible material and a heat-dispersible material while being consumed which is foldable onto itself, and when folded can be displayed for sale in compact form.

The aforesaid primary objects and other objects are alternatively accomplished by providing a package containing a mixture of a heat-dispersible material and a combustible material, and a support device for the package in one of two alternative forms. The first form of the device requires hand assembly for the user. This device is made from a single, rectangular sheetmetal blank which is stamped, photoetched, or perforated to produce a foldable design blank for a package holder. For convenience of description, these various alternative procedures of working the blank will collectively be referred to as being etched. The etched sheetmetal blank when unassembled is flat having a center section across the entire width of the sheet bordered by two etched lines. Two end sections extend from the etched lines defining the center section, each comprising an interior or inner portion having perforations therethrough and an outer portion bounding the inner portions. The inner portions are foldable upward from the two etched centerlines until they are spaced-apart in parallel relationship by the distance between the two centerlines. The combustible package containing the dispersible material and combustible material is held between these upwardly extending parallel sections in a sandwich-like manner. The perforations and side openings between the two parallel sections allow for free circulation of air so that the dispersible material is readily dispersed. The side openings permit easy access for ignition of the package by a match or lighter. The outer portion of the end sections surrounding the inner portions are folded downward from the etched centerlines to form legs to support a package. The end of each outer portion is folded at an angle at the etched end lines so that the ends will sit flat upon the surface on which the support rests. The space between the center section holding the package and the surface carrying the device permitting free circulation of air prevents heat build-up and damage to the surface carrying the device. The device is reusable.

The second form of the device of the present invention comprises a folding paperboard package utilized in conjunction with the device formed from the blank as described hereinabove. In this form the device is pre-assembled and the legs of the device separated by a fold-line are attached to the paperboard so as to automatically unfold and set up when the paperboard package is unfolded. The inside surface of the folding paperboard package can be foil covered to reflect the heat of the package being consumed and protect the surface on which the device when in use is seated. This device is also reusable.

Having described the invention in general terms, presently preferred embodiments will be described in reference to the drawing.

DRAWING AND PRESENTLY PREFERRED EMBODIMENT

In the drawing,

FIG. 1 is a top view of a blank for fabricating a device for holding a combustible package containing a heat-dispersible material and a combustible material while being consumed according to a first form of the present invention;

FIG. 2 is a side view of the device fabricated from the blank of FIG. 1 in assembled form;

FIG. 3 is a perspective view of the assembled device of FIG. 1 supporting a combustible package;

FIG. 4 is a perspective view of a device for holding a combustible package of a heat-dispersible material and a conbustible material according to a second form of the present invention in the folded condition for arrangement on a display rack;

FIG. 5 is a side sectional view of the device of FIG. 4 still in the folded condition taken along line 5—5 of FIG. 4;

FIG. 6 is a side view of the device of FIG. 4 in the unfolded or operative condition;

FIG. 7 is a perspective view of the device of FIG. 4 in the unfolded or operative condition with one section of the device broken-away.

Figure 8:
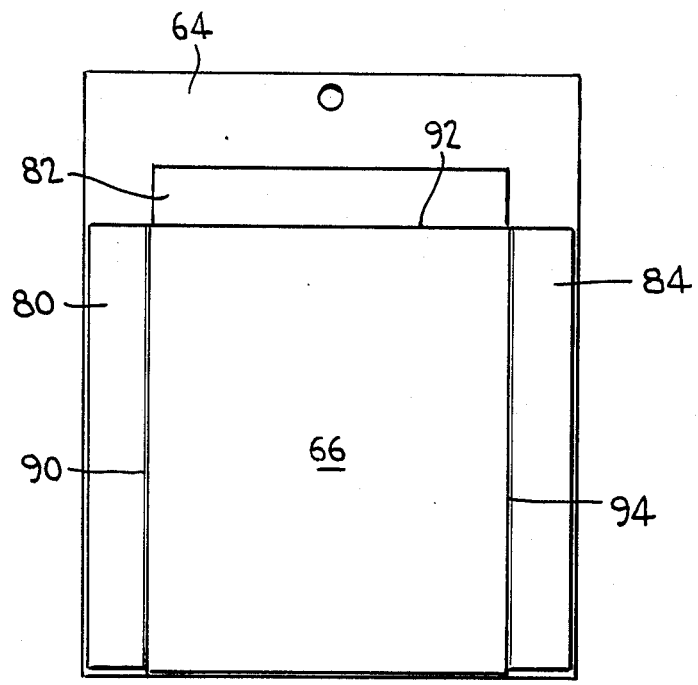
FIG. 8 is a front view of the device of FIG. 4 still in the folded condition.

The form of the device of the present invention shown in FIGS. 1-3 comprises a flat, rectangular sheetmetal blank 10 for hand assembly by the user. The blank as shown in FIG. 1 has a center section 12 defined by etched centerlines 14 and 16, and first and second end sections 18 and 20. End sections 18 and 20 are mirror images of each other and comprise internal or inner sections 22 and external or outer sections 24. Inner sections 22 are completely separated from outer sections 24, but inner sections 22 and outer sections 24 are fixedly joined to center section 12 at etched centerlines 14 and 16. Also as shown in FIG. 1, each of inner sections 22 have perforations 25 and etched side fold-lines 26 and 28 which, when folded in, form sides 30 and 32. Finally, each of outer sections 24 have tabs 34 and end etch lines 36 substantially coextensive with the end of inner sections 22. Blank 10 is readily assembled into a support device by folding inner sections 22 upward from centerlines 14, 16 as shown in FIGS. 2 and 3. Inner section 22 is also folded in along etch lines 26, 28 to form sides 30, 32. Outer sections 24 are folded downward at a slant from etched centerlines 14, 16 to form legs 23, and then outward along end etch lines 36 to form feet 38. Feet 38 in cooperation with tabs 34 stabilize the device so that the device will stand on a flat surface with spaced center section 12 spaced substantially above the flat surface, permitting free air circulation. The distance that centerspace 12 will be spaced above the carrier surface can be controlled to a limited extent depending upon the slant at which the outer portions 24 are folded from the centerline to form legs 23.

A package 50 is placed in space 52 between parallel inner sections 22. The package when positioned in the support device is easily ignited with a match or lighter so as to consume the package and disperse the heat-dispersible material as a vapor. The heat-dispersible material will readily flow through perforations 25 as well as through the side and top of space 52 between parallel inner sections 22.

A second and alternative form of the invention is illustrated in FIGS. 4–8. In this form of the invention, the device of FIGS. 1–3 is assembled as hereinbefore described. Feet 38 and tabs 34 are then fixedly secured using any conventional means such as an adhesive to a paperboard member 60 having a substantially flat surface except for an area having an inverted V-fold 62. Feet 38 straddle the V-fold. The paperboard as shown in FIGS. 4–8 extends in each direction from V-fold 62 to form a first paperboard section 64 and a second section 66. As illustrated, section 64 is longer than section 66 and has a hole 68 for hanging the device on a display rack. Further as shown in FIGS. 4–8, section 66 is sealed to section 64 by three glue flaps 80, 82, and 84. Section 66 is attached to the glue flaps by three sections 90, 92 and 94, section 94 not being shown. Sections 90, 92, and 94 may be joined to section 66 and glue flaps 80, 82, and 84 by perforations 100 and 102 to enable sections 90, 92, and 94 to be removed as by pulling on pull tab 96.

As will be apparent, however, it is possible to construct the device wherein sections 64, 66 are of the same length with a hole passing through each of the end sections to permit hanging of the device on a display rack. Also, it is possible to connect sections 64 and 66 by removable opening means other than sections 90, 92 and 94, and have opening means other than pull tab 96 and perforations 100 and 102.

As shown in FIG. 7, in the cut-away section paperboard 70 is covered with a metal foil 72 to provide a reflective surface to reflect heat generated on combustion of package 50 away from furniture or other surface upon which the device rests during combustion.

The form of the invention shown in FIGS. 1–3 which consists of a single piece of flat, rectangular sheetmetal which, in a preferred embodiment is approximately five and one-half (5½") inches long, approximately three (3") inches wide and 0.007 to 0.010 inches in thickness, is sold to the consumer as a blank along with a package 50 containing the heat-dispersible material. Accordingly, before use the consumer will construct the device by folding up the inner sections 22 along etched centerlines 14 and 16, and folding down outer sections 24 to form downwardly extending legs 23, and then folding out feet 38 to provide a standing surface. In this form the device provides a convenient means of confining a combustible package which is to be consumed safely yet allowing free release of smoke through openings 25. The device provides sufficient air space under the burning package because of legs 23 to prevent scorching of a counter or table surface upon which the device is used. The device which is reusable provides ease of access for match or lighter ignition.

As will be apparent to one skilled in the art, the heat-dispersible material can be any material which is desirably vaporized during use such as a fungicide, insecticide, antiseptic, deodorant, or other materials commonly used to fumigate or otherwise treat a closed environment. The combustible package containing the heat-dispersible material can include additive materials known in the art, such as a gas-generating or blowing substance or consumable heat-generating materials, to enhance dispersion of the heat-dispersible material into the environment. Packages of this type are known in the art including in the art cited hereinbefore, which teachings are incorporated herein by reference.

The form of the invention shown in FIGS. 4–8 is pre-assembled but is in folded form at the time it is sold to the consumer. The folded device can be placed in usable or operable form by simply unfolding the paperboard holder along the V-fold 62. A package 50 is preferably in the device when sold to the consumer and, accordingly, it is not necessary for the user to insert a package at the time of use. As shown in the embodiment of FIG. 7, the paperboard is covered with a metal foil to help reflect heat upward and to further protect the surface upon which the device is seated. The device is easily displayed and can include directions for its use on the surface of the paperboard which is exposed when in the folded condition. To open the package, the user pulls on pull tab 96 to remove sections 90, 92, and 94. Sections 64 and 66 can then be unfolded to set up the assembly. The flat paperboard surfaces upon which the device is affixed help to maintain the device flat and immobile. As is apparent, it is not necessary for the consumer to construct the assembly from blank 10 as in the first form of the invention. While paperboard is preferably used according to the invention, it is also possible to utilize a plastic or even a lightweight metal. However, the use of such materials will increase the expense of the device. As in the first form, the device is reusable, with it only being necessary to purchase replacement packages 50 for subsequent use.

As will be apparent to one skilled in the art, various modifications can be made within the scope of the aforesaid description. Such modifications being within the ability of one skilled in the art form a part of the present invention and are embraced by the appended claims.

It is claimed:

1. A device fabricated from a single rectangular sheetmetal blank for supporting a combustible package containing a heat dispersible material and a combustible material, the combustible package to be consumed while being supported in said device, said sheetmetal blank comprising an outer frame having the general shape of the number eight, said frame further comprising a central section defined by two spaced apart central scorelines extending across the width of the sheetmetal blank; two essentially U-shaped mirror image outer sections, extending outwards from the central section, each joined to the center section at two locations at the opposite ends of the center section forming the general shape of the number eight; and two essentially rectangular mirror image inner sections joined to the frame along the center scorelines of the center section, said sections each being bounded by, but unattached to, the respective outer sections of the frame along three sides and attached to the center section of the frame on a fourth side along a center scoreline, said support device being fabricated by folding said inner sections upwardly along the center scoreline into a parallel relationship with each other, thereby forming a compartment and folding the outer sections of the frame downward along the centerlines to form an oblique angle with the inner sections and form thereby a pair of legs for supporting the compartment.

2. The device of claim 1 wherein said inner sections include a side scoreline along each side thereof and perforations between said side scoreline, and in fabrication of the device the inner sections are folded inwardly along each of said side scoreline.

3. The device of claim 2 wherein said outer sections include end scorelines across the width of the blank where the sides of the outer sections join with the ends of said outer sections, and in fabrication of the device the ends of said outer portions are folded outward along said end scoreline to form feet for stabilizing said device.

4. The device of claim 3 wherein the ends of said outer sections include integral center tabs taken from material of said inner sections, whereby in fabrication of said device said center tabs extend inwardly in the same plane as said feet to further stabilize said device.

5. In combination, the device of claim 4 and a combustible package of heat-dispersible material and combustible material supported between said parallel inner sections.

6. In combination, the device of claim 4 and a rectangular support therefor, said rectangular support having a top surface with said top surface having a fold area and end sections extending from said fold area, said feet of said device being fixedly attached to said top surface so as to straddle said fold area, said combination being foldable upon itself to provide a compact display unit.

7. The combination of claim 6 wherein said rectangular support is paperboard.

8. A rectangular sheetmetal blank for forming into a support for a combustible package containing a heat dispersible material and a combustible material comprising an outer frame having the general shape of the number eight, said frame further comprising a central section defined by two spaced apart central scorelines, extending across the width of the sheetmetal blank; two essentially U-shaped mirror image outer sections, extending outwards from the central section, each joined to the central section at two locations at the opposite ends of the central section forming the general shape of the number eight; and two essentially rectangular mirror image inner sections joined to the frame along the central scoreline of the central area, said sections each being bounded by, but unattached to, the respective outer sections of the frame along three sides and attached to the central section of the frame on a fourth side along a central scoreline, said support device being fabricated by folding said inner sections upwardly along the central scoreline into a parallel relationship with each other thereby forming a compartment and folding the outer sections of the frame downward along the centerlines to form an oblique angle with the inner sections and form thereby a pair of legs for supporting the compartment.

9. The blank of claim 8 wherein said inner section include a side scoreline along each side thereof and perforations between said side scorelines, and in fabrication of the device, the inner sections are folded inwardly along each of said side scorelines.

10. The blank of claim 9 wherein said outer sections include end scorelines across the width of the blank where the sides of the outer sections join with the ends of said outer portions, and in fabrication of the device the ends of said outer sections is folded outward along said end scorelines to form feet for stabilizing said device.

11. The blank of claim 10 wherein the ends of said outer sections include integral center tabs taken from material of said inner sections, whereby in fabrication of said device said center tabs extend inwardly in the same plane as said feet to further stabilize said device.

12. An article of manufacture comprising in combination a rectangular base having a central fold area extending across said base, end sections extending in each direction away from said fold area, and a device for supporting a combustible package containing a heat dispersible material and a combustible material, the combustible package to be consumed while being supported in said device, said device further comprising a single rectangular sheetmetal blank further comprising an outer frame having the general shape of the number eight, said frame further comprising a central section, defined by the two spaced apart central scorelines, extending across the width of the sheetmetal blank; two essentially U-shaped mirror image outer sections extending outwards from the central section each joined to the central section at two locations at the opposite ends of the central section forming the general shape of the number eight; and two essentially rectangular mirror image inner sections joined to the frame along the central scorelines of the central section, said inner sections each being bounded by, but unattached to, the respective outer sections of the frame along three sides and attached to the central sections of the frame on a fourth side along a central scoreline said support device being fabricated by folding said inner sections upwardly along the central scoreline into a parallel relationship with each other thereby forming a compartment and folding the outer sections of the frame downward along the centerlines to form an oblique angle with the inner sections and form thereby a pair of legs for supporting the compartment, said feet being fixedly attached to said rectangular base, one of said feet being located on each side of said foldline, said combination being constructed and arranged whereby when said rectangular base is folded onto itself at said fold area, said device also folds on to itself with said feet being parallel to said legs to form a compact unit of substantially the same thickness as the width of the center section of the device.

13. The article of manufacture of claim 12 wherein said rectangular base is paperboard.

14. The article of manufacture of claim 12 further including in said combination a combustible package containing a heat-dispersible material and a combustible material supported between said parallel inner sections.

15. The article of manufacture of claim 12 wherein said fold area is an inverted V-fold.

16. The article of manufacture of claim 15 wherein said end sections of said rectangular base are joined together by removable opening means.

17. The article of manufacture of claim 15 wherein said central fold area divides the rectangular base into sections of different lengths, with the longer length having a hole at the upper center thereof which permits hanging said article of manufacture as a display.

18. The article of manufacture of claim 17 wherein said paperboard rectangular base has a reflective metal foil on the inner side which is folded onto itself.

19. The article of manufacture of claim 18 wherein said inner sections include side scorelines along each side thereof and perforations between said side scorelines, said inner sections being folded inwardly along each of said side scorelines.

20. The article of manufacture of claim 19 wherein the ends of said outer sections include integral center tabs taken from material of said inner sections, and said center tabs extend inwardly in the same plane as said feet, with said tabs being fixedly attached to said rectangular surface.

* * * * *